US008992855B2

(12) United States Patent
Lin (10) Patent No.: US 8,992,855 B2
(45) Date of Patent: Mar. 31, 2015

(54) LOW VOLUME LIQUID SPECIMEN APPORTIONMENT DEVICE

(76) Inventor: James Lin, San Diego, CA (US)

(*) Notice: Subject to any disclaimer, the term of this patent is extended or adjusted under 35 U.S.C. 154(b) by 677 days.

(21) Appl. No.: 13/014,222

(22) Filed: Jan. 26, 2011

(65) Prior Publication Data

US 2012/0190122 A1 Jul. 26, 2012

(51) Int. Cl.
*G01N 33/00* (2006.01)
*A61B 10/00* (2006.01)
*B01L 3/00* (2006.01)

(52) U.S. Cl.
CPC ............. *A61B 10/0096* (2013.01); *B01L 3/502* (2013.01); *B01L 2300/042* (2013.01); *B01L 2300/049* (2013.01); *B01L 2300/0663* (2013.01); *B01L 2300/0832* (2013.01); *B01L 2300/0864* (2013.01); *B01L 2400/0644* (2013.01)
USPC ........... 422/405; 422/68.1; 422/420; 422/561

(58) Field of Classification Search
USPC ................................. 422/405, 68.1, 420, 561
See application file for complete search history.

(56) References Cited

U.S. PATENT DOCUMENTS

| 5,119,830 A | 6/1992 | Davis |
| 5,403,551 A | 4/1995 | Galloway et al. |
| 5,976,895 A | 11/1999 | Cipkowski |
| 6,277,646 B1 | 8/2001 | Guirguis et al. |
| 6,726,879 B2 | 4/2004 | Ng et al. |
| 7,300,633 B2 | 11/2007 | Hudak et al. |
| 7,438,852 B2 | 10/2008 | Tung et al. |
| 7,758,815 B2 | 7/2010 | Hartselle |
| 2010/0028981 A1 | 2/2010 | Ramsey et al. |

*Primary Examiner* — Sam P Siefke
(74) *Attorney, Agent, or Firm* — Charmasson, Buchaca & Leach, LLP (57) ABSTRACT

A liquid specimen collecting and testing device has two chambers, a first for collecting a liquid specimen and a second for exposing a measured volume preliminary screening aliquot of the specimen to preliminary screening test strips. The first chamber has a catch basin of defined volume which is less than the sample volume. The basin is simultaneously sealed from the rest of the first chamber, thus separating and apportioning the measured volume preliminary screening aliquot from the collected volume. Simultaneously, an opening made leading from the basin to the second chamber initiating the preliminary screening test. Thus intermingling of a preliminary screening aliquot and a remainder aliquot is avoided.

12 Claims, 8 Drawing Sheets

LOW VOLUME LIQUID SPECIMEN APPORTIONMENT DEVICE

FIELD OF THE INVENTION

This invention relates generally to fluid specimen containers, testing devices for conducting preliminary chromatographic reaction screening tests, and more particularly to sealed receptacles for holding a separate aliquot of specimen for later confirmatory testing.

BACKGROUND

Fluid specimen cups are commonly used to collect and test fluid specimens for the presence or absence of specific "indicators" which show the presence of specific chemicals, hormones, antibodies or antigens and are commonly used for drug screening.

Collecting and testing fluid specimens carries a health risk for the person conducting the test and a contamination risk to the specimen or testing media. With a potential for contact with the sample by the operator or technician and its associated health and contamination risks, a sealed receptacle for preventing such contact is desirable. Testing devices as disclosed in Cipkowski U.S. Pat. No. 5,976,895 have required that a liquid specimen be placed in a specimen cup and that a technician manually insert and submerge a portion of a testing strip cartridge into the specimen through a narrow insertion slot. Liquid specimen can still spill through the slot, and a film of liquid specimen can remain on the cartridge if and when it is removed from the cup.

Various devices, such as that shown in Davis U.S. Pat. No. 5,119,830, show further reduction in the risk of contact by using chromatographic testing strips mounted in substantially sealed cup lid. The initiation of the testing procedure may be controlled by activating a frangible partition allowing passage of the fluid from the cup into a chamber in the lid containing the chromatographic test strip.

U.S. Pat. No. 5,403,551 Galloway requires inversion of the cup to an unspecified angle making adequate submersion of the test strips uncertain. Further, testing chambers that allow the flow of fluid onto the test strip upon inversion also allow the fluid to escape upon righting. Such action can inhibit the capillary action required in some test strips. Testing accuracy is often enhanced by proper orientation and immersion of the strips into the proper depth of the fluid. Many prior devices do not provide for such control of the fluid depth, volume and strip orientation. Some types of preliminary screening tests such as those directed toward detecting THC levels in urine often resulting from the use of marijuana require a minimum fluid depth to ensure an adequate level of accuracy. Thus there can often be a trade-off between retaining enough fluid for the confirmatory testing while devoting adequate fluid for preliminary screening.

Oftentimes, the results of a particular preliminary screening test will indicate that further more rigorous and accurate testing should occur. For example, if a preliminary screening test comes back positive for drug use, the conductors of the test may seek to conduct a more rigorous and accurate test to confirm the presence of the offending component. Such secondary testing is often referred to as confirmatory testing.

In many prior devices, the liquid specimen volume, as a whole, comes into contact with the test strip. That contact can change the chemical characteristics of the remaining specimen so that the confirmatory test cannot be performed on the fluid specimen as originally supplied by the donor. In other words, the portion of the specimen in contact with the strips is also capable of contacting and intermingling with the remainder of the specimen. Such intermingling can lead to contamination of the remaining sample to a degree which diminishes optimum further testing of that specimen.

In the past, this problem has been addressed by taking multiple liquid specimens potentially removed in time from when the original specimen was taken. One can easily appreciate that the taking of a subsequent specimen after a prolonged period allows for changes in the physiology of the test subject. For example, a person suspected of taking drugs can cease drug use whereupon tests taken days later may not turn up positive.

More recently, various specimen-collecting and testing cups such as those disclosed in Guirguis U.S. Pat. No. 6,277, 646 and Ng et al., U.S. Pat. No. 6,726,879 have been proposed that provide for two amounts of the specimen to be separated from one another. In this way, the first amount can be subjected to the test strips without contaminating the second, separated amount.

Such devices suffer from being bulky, difficult to operate, expensive to manufacture and provide less than adequate amounts of fluid for conducting the preliminary or confirmatory tests. For example, the device of Guirguis provides for only a limited or relatively uncontrolled amount or aliquot of fluid for preliminary testing, thereby making it potentially difficult to adequately contact the multiple strips or preserve enough of the sample for confirmatory testing. Also, the introduction of the aliquot can increase pressure in the test chamber to a degree which can effect test accuracy.

Some devices such as one disclosed in Hudak et al., U.S. Pat. No. 7,300,633 require multiple steps, one step to initiate the preliminary screening test and another step to seal one or both of the separated specimen amounts. Such multi-step processes can be confusing to unskilled workers and lead to mistakes in processing.

Many preliminary tests require viewing of the results within a specific time frame after the test has been initiated. Therefore, it is important for the test to remain uninitiate-able by the donor. This also helps avoid tampering by the donor. However, it is often impractical for the test to be initiated by a doctor or other highly skilled person. Increasingly, tests are being performed and evaluated by relatively unskilled technicians. Therefore, the device needs to be relatively simple to operate to insure adequate exposure of the test strip and to provide accurate results. Devices that require precise actions by the test conductor such as the proper orientation of the strips during testing are a source for additional error.

To avoid the contamination or even the appearance of contamination it is desirable to delay separation of the fluid sample into the two portions for as long as possible, preferably right up until the screening test is initiated. One problem with some of the above devices is that it separates the two portions early on, potentially well before testing needs to occur. This gives time for the two portions to be treated differently though unintentionally. For example, one portion may be subjected to slightly different heating or lighting conditions. One portion might be subjected to a greater surface area of the cup leading greater potential for interaction with the surface materials. Further, different portions of the cup may contain different materials, for example one portion may have contacted a rubber O-ring material. Although such materials are selected to be chemically inert, it is possible for those materials to have undergone some manufacturing mistake to carry contaminants. Though the probability of contamination may be small, and the amount of contamination minute, it may still be significant in some instances. Therefore, a design which minimizes the potential for contamination or differences between the two portions would be preferred.

It is also advantageous to maximize the volume of fluid preserved for confirmatory testing. This is because some types of confirmatory tests can require more fluid or the test may need to be repeated. In addition, a larger volume is often less susceptible to contamination by its environment by the mere fact that contaminant concentration is lower.

Because of the need to avoid contamination or even the appearance of possible contamination, it is desired that the specimen test cups be disposable. Therefore, to maintain low cost, it is important that efficient manufacturing methods, low cost materials and low cost designs are provided.

There is, therefore, a need for a specimen collection and preliminary screening cup which exhibits one or more of the following characteristics: insures proper testing by allowing the test strips to be in continuous and controlled contact with and adequate amount and depth of the liquid sample, to properly orient test strips, provides simple testing procedures, is inexpensive to manufacture, is flexible in accommodating different types of testing procedures, and provides for a maximized portion of the specimen volume to be uncontaminated by the testing process.

SUMMARY

The primary and secondary objects of the invention are to provide an improved fluid specimen collection, screening and confirmatory aliquot preservation. These and other objects are achieved by a cup having a measured volume preliminary aliquot apportionment structure.

The content of the original claims is incorporated herein by reference as summarizing features in one or more exemplary embodiments.

In some embodiments there is provided a liquid specimen collecting, apportioning and testing device comprises: a first sealable chamber, said chamber being shaped and dimensioned to have a basin portion of defined volume; said basin having a first opening and a second opening sealed by an openable barrier; a second sealable chamber containing a number of preliminary screening strips; a movable sealing and apportioning member shaped and dimensioned to seal said first opening; and, a barrier opener associated with said movable sealing member, said opener oriented to automatically open said barrier upon said movable sealing member sealing said first opening, thereby allowing fluid in said basin to flow into said second chamber and contact said strips.

In some embodiments the device further comprises said first chamber having an opening sealable by a lid.

In some embodiments said sealing member is connected to said lid, whereby movement of said lid causes movement of said sealing member.

In some embodiments said first chamber comprises a non-planar bottom portion having a section shaped to form said basin.

In some embodiments said basin is substantially cylindrically shaped and said sealing member comprises a piston having a substantially circular face dimensioned to intimately engage said basin.

In some embodiments said piston has a lower surface shaped and dimension to contact a commensurately shaped bottom surface of said basin.

In some embodiments said piston fully engaging said basin decreases the volume of said basin by said first volume.

In some embodiments said opener comprises a spike extending axially from said piston, wherein said spike has a first axial length selected to allow penetration of said barrier after said piston has sealed said first opening.

In some embodiments said second chamber is shaped and dimensioned to have a well located axially below said second opening; and wherein said spike is further shaped to nestingly mate with said well when said piston has fully engaged said basin.

In some embodiments said device comprises an inner vessel and an outer vessel, wherein said second chamber is formed between an inner surface of said outer vessel and an outer surface of said inner vessel; and wherein said strips are carried within a number of channels formed between said inner surface and said outer surface.

In some embodiments a sealable vent is formed between said second chamber and the outside of said device.

In some embodiments the device further comprises an annular wall extending coaxially downward from an undersurface of said lid, said wall having an outer diameter commensurate with an inner diameter of said inner vessel.

In some embodiments there is provided a method for conducting a fluid specimen test comprises: selecting a vessel having a first chamber and a second chamber in fluid communication with said first chamber, wherein said first chamber has a basin having a defined volume; introducing an amount of fluid into said vessel wherein said first amount is larger than said defined volume and said basin is filled with an aliquot of said amount; simultaneously separating and apportioning said aliquot from said first amount and initiating a preliminary screening test using said aliquot.

In some embodiments said separating and apportioning comprises sealing a first opening of said basin.

In some embodiments said initiating comprises opening a second opening in said basin.

In some embodiments said initiating further comprises forcing said aliquot from said basin.

DESCRIPTION OF THE EXEMPLARY EMBODIMENTS

Figure 1:
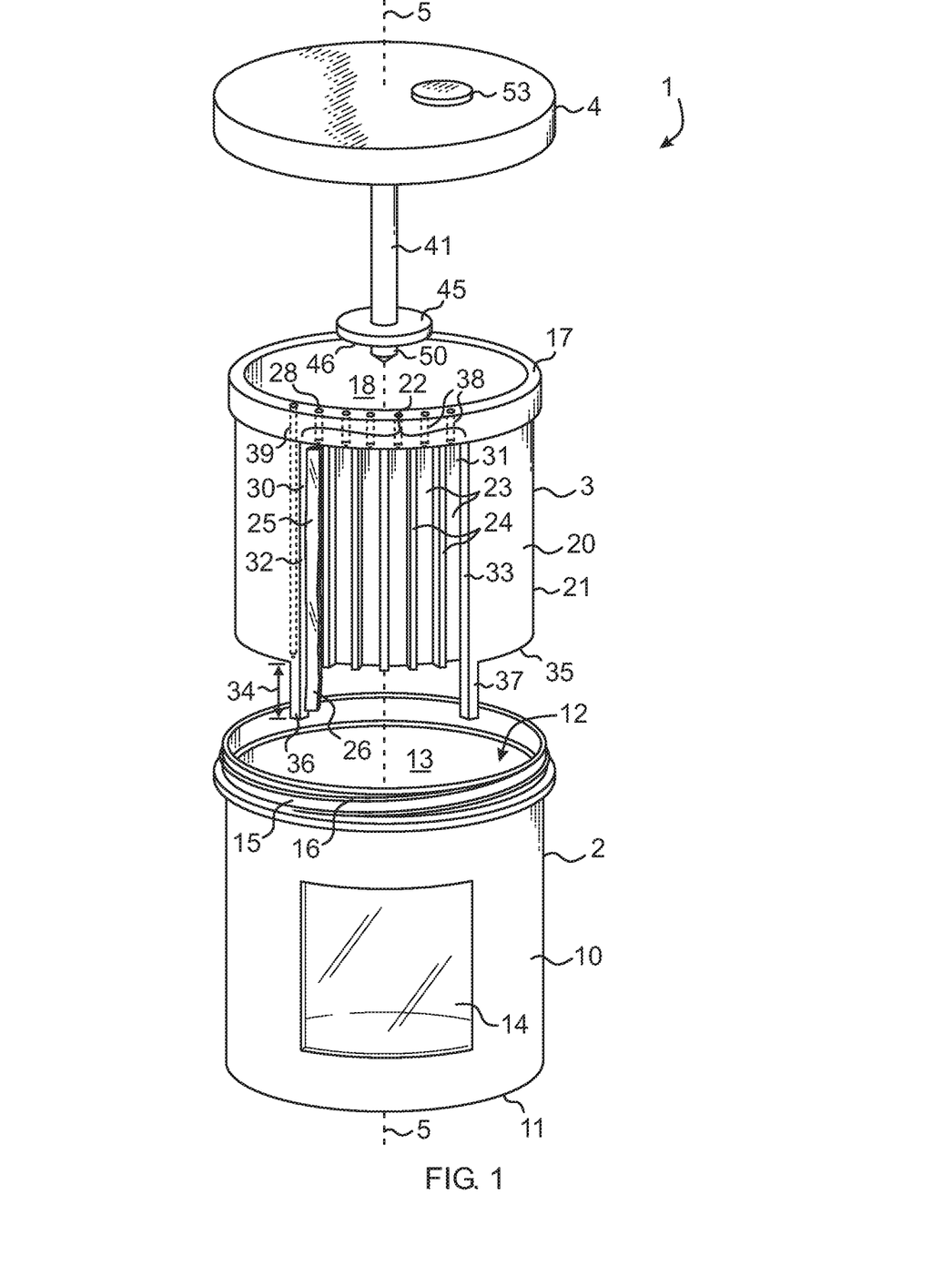
FIG. 1 is a diagrammatic exploded perspective view of a liquid specimen collection, preliminary screening, and confirmatory aliquot preservation device.
Figure 2:
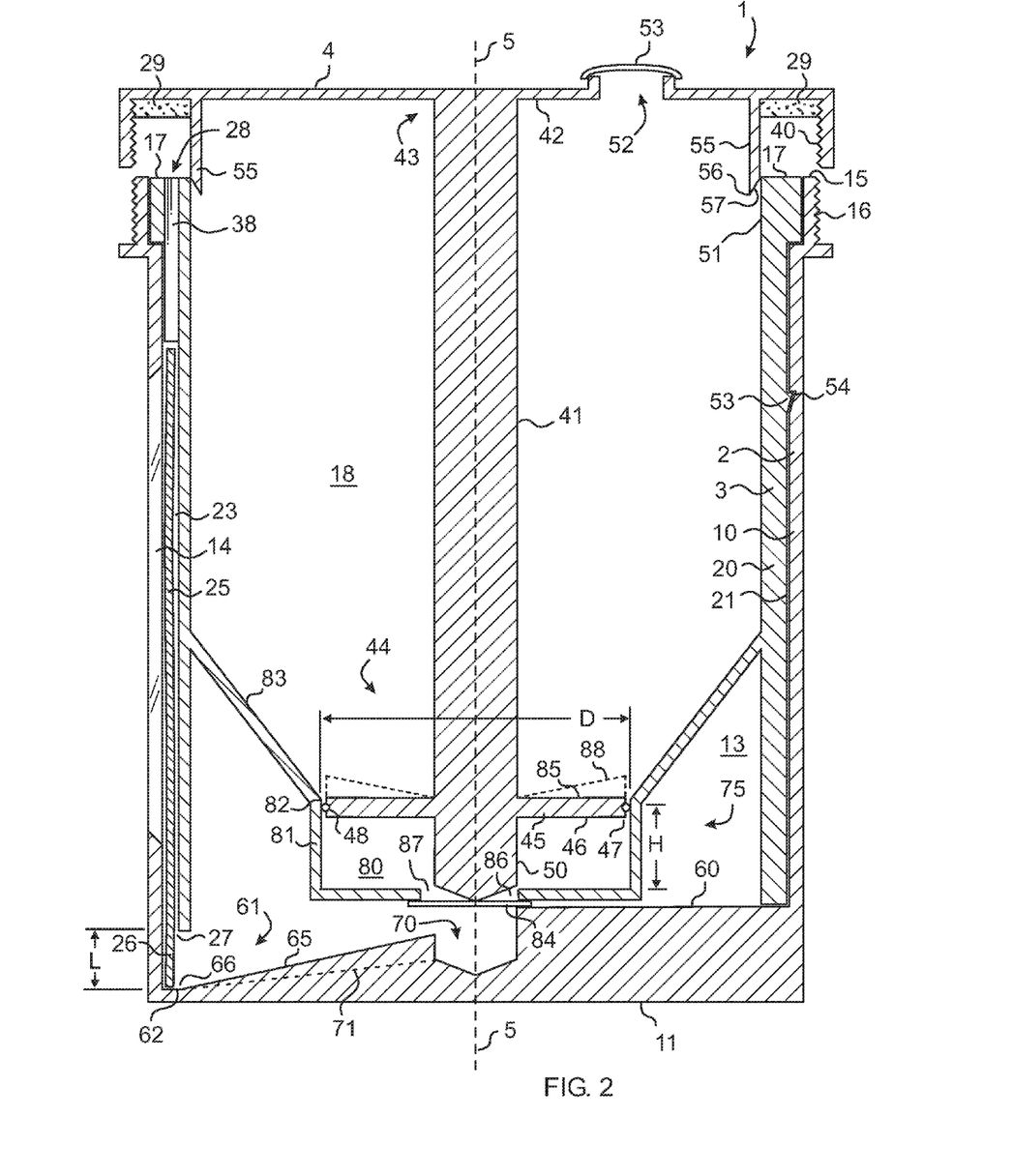
FIG. 2 is a diagrammatic cross-sectional side view of the device of FIG. 1.

Referring now to the drawing, there is shown in FIGS. 1-2, a fluid specimen collection cup 1 having an first outer vessel 2, a second inner vessel 3 and a top sealing lid 4. Both vessels and lid are shaped and dimensioned to mate along a common axis 5.

The outer vessel 2 has a substantially cylindrical side wall 10, a substantially circular bottom 11, and a substantially circular top opening 12 leading to a substantially cylindrical internal cavity 13. A viewing window 14 made of transparent material is formed into a portion of the sidewall providing visual access through the sidewall. It should be noted that the entire outer vessel can be made of transparent material in which case the window would be integral with the other portions of the outer vessel. The upper peripheral rim 15 of the outer vessel is threaded 16 to screwingly secure the top sealing lid 4.

The inner vessel 3 has a substantially cylindrical side wall 20 having a circular top opening leading to an internal cavity 18 which forms a first chamber of the cup. The side wall has an outer surface 21 shaped and dimensioned to be intimately inserted into and nest within the internal cavity 13 of the outer vessel 2 and to be contained therein. In other words, the outer surface of the inner vessel side wall is commensurate with the inner surface of the outer vessel side wall. An arcuate array 22 of parallelly spaced apart, oblong, substantially vertical channels 23 are formed into the substantially cylindrical outer surface of the inner vessel. Adjacent channels are separated from one another by vertical ribs 24. Each channel is shaped and dimensioned to contain a single chromatographic testing strip 25 therein so that the indicator lines of each strip face outward. Only one strip is shown populating the left-most channel 30 in FIG. 1. Once the inner vessel 3 is mated to the outer vessel 2 the array of channels and thus any contained strips are essentially closed off but for a lower aperture 27 (shown in FIG. 2) through which a bottom portion of the strips protrude, and pressure equalization vents 38,39 described below. The strips are oriented in the channels to be viewed through the front viewing window 14. The two lateral-most channels 30,31 are bordered by a pair of ridges 32,33 which extends downwardly a distance 34 below the bottom edge 35 of the inner vessel to form a pair of support legs 36,37 whose purpose will be described below. Air pressure equalizing vents 38 can be formed between one or more of the channels and the top rim 17 of the inner vessel. In addition or alternately, one or more longer air pressure equalizing vents 39 can extend axially between the bottom edge and top rim of the inner vessel.

The substantially cylindrical lid 4 has inner thread 40 commensurate with threads 16 formed onto the upper rim 15 of the outer vessel 2. This allows for the lid to be screwingly secured to the top of the outer vessel and thus seal it. A washer 29 made from a resilient material such as rubber is located peripherally inward from the lid rim and oriented to simultaneously seal the upper rims of both the inner and outer vessels when the lid is fully secured to the cup. The washer also blocks the exit ports 28 for any pressure equalizing vents 38,39.

A central rod 41 extends axially downwardly from the undersurface 42 of the lid. The rod 41 is connected at a proximal end 43 to the lid 4. An opposite distal end 44 carries a substantially cylindrical, disk-shaped piston structure 45 having a substantially circular lower face 46, and spaced an axial distance apart from the distal tip of a distal spike 50. The operation of the piston and spike will be described below. Although shown to be substantially cylindrical and solid, the central rod between the piston and lid can have other shapes to reduce material or manufacturing costs while maintaining adequate rigidity. For example, the rod can be hollow having a circular cross section taken perpendicular to the axis. Or, for another example, the rod can have a cross-shaped cross-section.

An access aperture 52 through the lid is releasably sealed by a cap 53. The aperture is sized to allow penetration of a pipette or other oblong implement therethrough to access a preserved portion of sample fluid remaining in the first chamber for confirmatory testing.

Referring now primarily to FIG. 2, there is shown a cross-sectional view of the cup 1 where the inner vessel 3 is fully seated within the outer vessel 2, and the lid 4 is in the process of being engaged upon the upper rim 15.

The lid 4 is further adapted to have a generally cylindrically shaped internal annular wall 55 extending axially downwardly from the lid undersurface 42 and located coaxially with the rod 41 so that alignment is maintained during twisting motion of the lid relative to the cup. The lower distal lip 56 of the wall 55 can have an inwardly angled frusto-conically-shaped surface 57 to allow the wall to be guided into the top opening of the inner vessel 3. The outer diameter of the wall is commensurate with the inner diameter of the top opening 51 of the inner vessel 3 so that when the lid engages the device, the wall intimately engages the inner vessel thereby sealing it before the lid is fully engaged upon the device. This sealing prevents liquid from escaping prior to the initiation of the preliminary screening test. This also acts as a secondary seal for the entire cup after the preliminary screening has been completed.

It shall be noted that the axial length of the internal annular wall 55 of the lid 4 can be selected so that the lower distal lip 56 of the wall does not contact the inner vessel 3 until the piston structure 45 has sealed the circular top opening 82 of the catch basin 80 as will be described below. This simultaneous sealing of the lid annular wall 55 against the inner vessel and the piston against the catch basin of the inner vessel helps maintain ambient pressure inside the internal cavity 18 of the inner vessel.

A locking nib 53 extends outwardly from the outer surface 21 of the side wall 20 of the inner vessel 3 to engage a corresponding recess 54 set into the inner surface of the side wall 10 of the outer vessel 2 to securely lock the vessels together.

Figure 3:
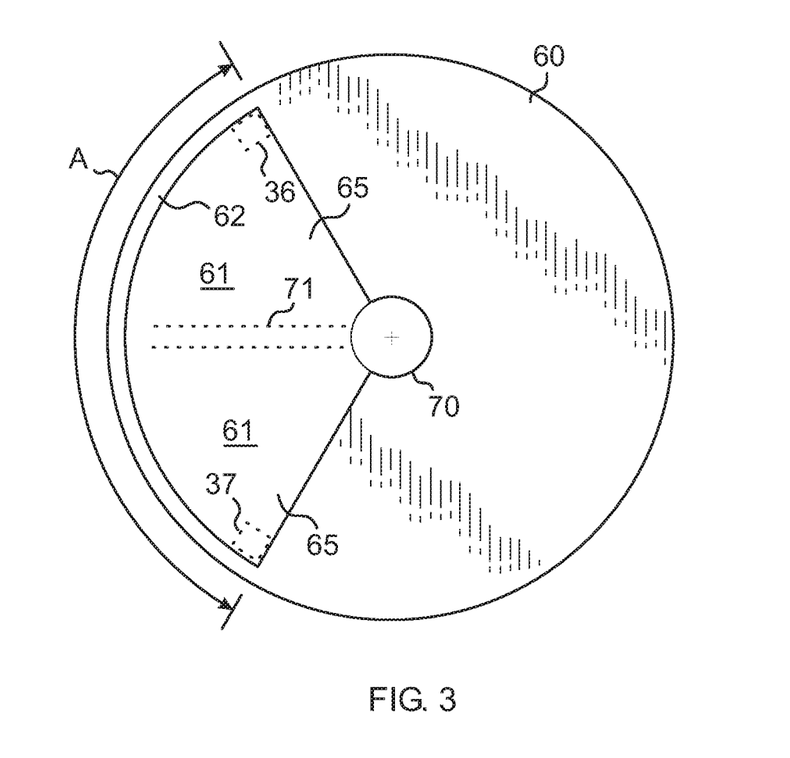
FIG. 3 is a diagrammatic top view of the floor of the outer vessel.

The floor 60 of the outer vessel 2 is shaped and dimensioned to form a generally wedge-shaped, second chamber 61 when viewed from above in FIG. 3 covering an angle A which accommodates all of the strips in the array 22 of channels. The second chamber accepts the preliminary screening aliquot once the preliminary screening test is initiated. The lateral legs 36,37 of the inner vessel 3 extend into and contact the bottom surface 62 of the outer vessel to support the chromatographic testing strips 25 in a manner which allows the lower dangling ends 26 to penetrate a length L into the second chamber and the pool formed by the preliminary screening aliquot pooled in the chamber. The length is selected to allow the strip ends to be immersed in the pooled liquid to a minimum adequate depth for the one strip requiring the most depth for proper testing. The legs are located at the angular periphery of the chamber to angularly locate the array of channels against the viewing window.

A substantially wedge-shaped ramp 65 leads downwardly and radially outwardly toward a radially peripheral arcuate pool 66 where the ends of the strips are located. The ramp reduces the volume of the chamber while causing liquid to flow toward the pool under the effect of gravity alone. This structure is dimensioned to maintain an adequate depth of fluid in the pool for those types of strips requiring a minimum depth. The radially central part of the chamber forms a substantially cylindrical collection well 70 located axially in the center of the floor 60. The well is dimensioned to be intimately engaged by the spike 50 when the lid 4 is fully seated.

An optional groove 71 is cut into the ramp leading from the well to the pool to facilitate flow of fluid from the well toward the peripheral pool. The full penetration of the spike into the well further minimizes the required volume of the preliminary screening aliquot. It shall be understood that the inner vessel is angularly oriented with respect to the outer vessel so that all of the strips held by the array of channels are inserted into the pool.

The bottom 75 of the inner vessel 3 is formed to have a centrally located catch basin 80 having cylindrical side wall 81 and a circular top opening 82 surrounded by an angled, frusto-conical peripheral flange 83 to facilitate aligned insertion of the piston and the flow of fluid toward the basin. In this way the basin is the primary destination of fluid entering the inner vessel so that an adequate amount of preliminary screening aliquot is ensured is such an amount has been deposited in the cup. A circular central bottom hole 86 is sealed by a frangible barrier 84 such as plastic-coated aluminum foil. The barrier is broken by the penetrating spike 50. A radial dimension of the hole is larger than the diameter of the spike so that the spike does not seal the hole as it passes therethrough leaving a gap 87. It this way the fluid in the basin can pass through the gap while the spike penetrates into the hole.

Alternately, the spike can be shaped to intimately engage the hole and have a radial notch to allow for passage of fluid therethrough. However, the existence of a notch could lead to the trapping of an amount of fluid therein. Therefore, to minimize the volume of the required preliminary screening aliquot, the spike is selected to have an axially symmetric outer surface so that it fully nests within a commensurately shaped well thus forcing any liquid out of the well once fully engaged.

The height H and diameter D of the basin is selected to define the volume of the preliminary screening aliquot. As will be shown below, once the piston is fully inserted, the portion of the basin located above the top surface 85 of the piston forms a reservoir at the bottom of the first chamber for trapping the remainder aliquot. Alternately, the top surface of the piston can have a substantially conical shape as shown by the dotted line 88. In this way the lowermost portion of the reservoir has a substantially conical shape to cause the remainder aliquot to collect against the rod 41 in the center of the first chamber. In this way the depth of the remainder aliquot is increased facilitating easier access by a pipette during confirmatory testing. Such a shape also stiffens the piston structure so that it maintains its shape during the apportionment process. The lower face 46 of the piston structure is shaped and dimensioned to be commensurate with the bottom basin so that essentially all of the fluid trapped in the basin below the piston is forced out into the second chamber. In order for the shapes to remain commensurate the stiffness of the piston shape can be important.

The disk-shaped piston 45 carried by the central rod 41 of the lid 4 has a cylindrical peripheral edge 47 dimensioned to intimately engage the inner wall surface of the basin, thus acting as a sealing member to seal the basin from the rest of the first chamber. A peripheral O-ring 48 mounted to the edge ensures the seal therebetween.

It is thus appreciated that the bottom portions of both the inner and outer vessels are formed into structures which will allow the cup to keep the liquid sample as a contiguous volume until the preliminary screening test is initiated whereupon the volume is apportioned into a first, metered volume portion referred to as a preliminary screening aliquot which is immediately flowed into a preliminary screening chamber, and a second, remainder volume portion, referred to as a remainder aliquot which is preserved for later confirmatory testing. The separation of the aliquots occurs simultaneously or nearly simultaneously with the initiation of the screening. This is important because it is impossible for the aliquots to later mix together. Also, the preliminary screening aliquot is funneled into a pool dimensioned to minimize the volume of the aliquot needed to ensure that all the strips have their ends immersed to an adequate depth. Because the preliminary screening aliquot is metered, a minimum volume can be selected to adequately fill the pool. In other words, only the amount of liquid necessary to conduct the preliminary screening is separated from the specimen provided by the donor. This leaves the maximum amount of specimen to be devoted to confirmatory testing.

Figure 4:
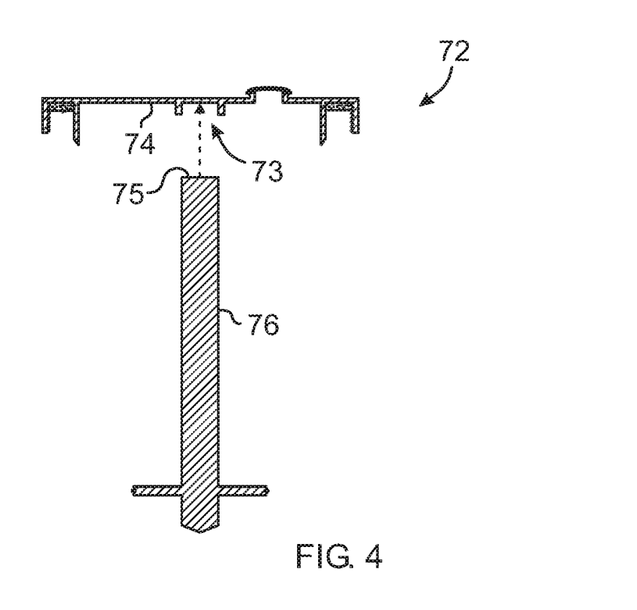
FIG. 4 is a diagrammatic cross-sectional side view of a lid having an attachable rod.

As shown in FIG. 4, a lid 72 can be provided having axial receptacle 73 in its undersurface 74 for securing the proximal end 75 of a rod 76 thereto. In this way, the lid without the rod secured can be given to the donor. The donor can collect the sample and screw on the lid without accidentally initiating the preliminary test. The technician can remove the lid, attach the rod, then resecure the lid to the cup to initiate the preliminary test.

Referring now to FIGS. 5-11, there is shown the various steps of conducting a preliminary screening and preservation of a confirmatory testing aliquot.

Figure 5:
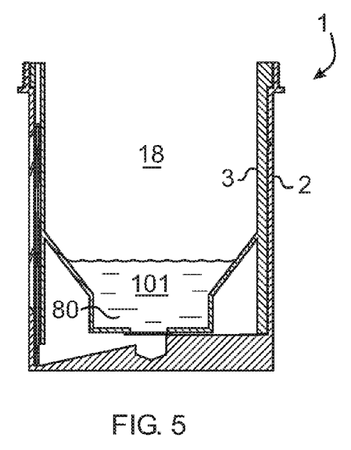
FIGS. 5-11 are diagrammatic cross-sectional side view of various stages in the preliminary screening process.

FIG. 5 shows a cup 1 having the inner vessel 3 mated to the outer vessel 2 and the lid removed. An amount of a fluid sample 101 is deposited into the internal cavity 18 of the inner vessel filling the basin 80.

Figure 6:
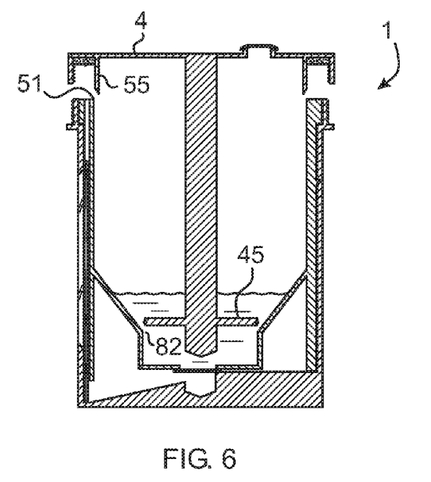

In FIG. 6 the lid 4 is starting to be placed on the cup 1. It's important to note that the annular wall 55 has not yet engaged the top opening 51 of the cup, and the piston structure 45 has not yet engaged the top opening 82 of the basin. The preliminary screening test has not yet been initiated and the two aliquots of fluid have not yet been separated or apportioned.

Figure 7:
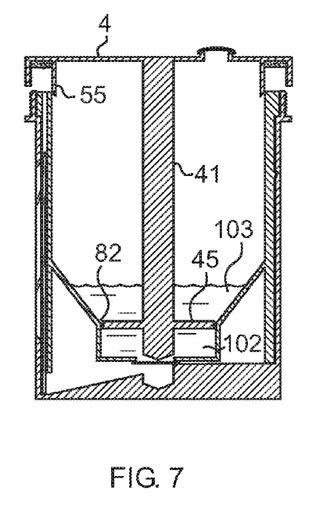

In FIG. 7, the lid 4 further engages the mated vessels so that the piston structure 45 at the distal end of the central rod 41 engages the top opening 82 of the basin. The o-ring located on the periphery of the piston forms a fluid seal between the piston and the basin wall. Thus the device has separated and apportioned the fluid sample into a first, metered volume preliminary screening aliquot 102 in the basin and a confirmatory testing aliquot 103 in the first chamber above the piston. The annular wall 55 has engaged the top opening of the cup sealing it. However, the preliminary screening test has not yet been initiated.

Figure 8:
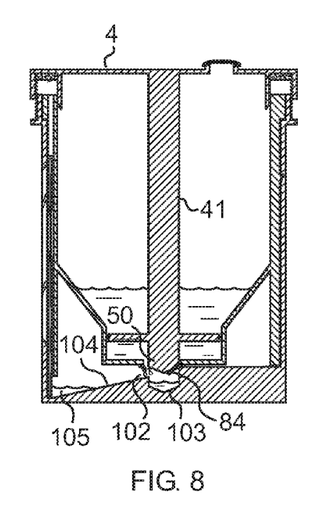

In FIG. 8, as the lid 4 is further screwed onto the vessels, the spike 50 on distal end of the rod 41 penetrates and breaks the frangible barrier 84 at the bottom of the basin. The basin now begins emptying the preliminary screening aliquot of fluid 102 through the now open gap and into the second chamber between the inner and outer vessels. Some of the preliminary screening aliquot has started to fill the central well 103 in the bottom of the outer vessel 2, while some has begun to flow down an angled ramp 104 to begin filling a radially peripheral distal pool 105 of the second chamber.

Figure 9:
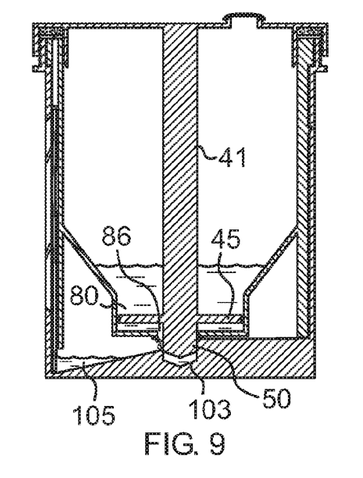

FIG. 9 shows further axial penetration of the piston structure 45 into the basin 80. The piston continues to drive the preliminary screening aliquot out of the basin through the open bottom hole 86. The distal spike 50 of the rod 41 has begun to intimately engage the bottom well 103 and force any collected liquid out of the well and into the pool 105.

Figure 10:
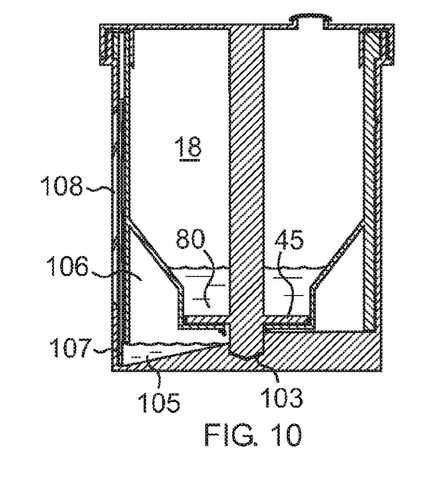

FIG. 10 shows the piston structure 45 fully engaging the basin 80, thus forcing all of the preliminary screening aliquot out of the basin and into the second chamber 106. Further, the spike, being shaped to intimately nest within the well 103, forces any fluid collected there out into the pool 105. Because preliminary screening aliquot is metered, the volume is known and thus forms an adequate depth of liquid in the pool, fully immersing the end 107 of the test strip extending into and dangling in the second chamber. After a time, the results of the preliminary screening test can be viewed through the from viewing window 108. Thereafter, the sealed cup can be stored and transported to a lab for confirmatory testing.

It is understood that the volume decrease in the inner vessel internal cavity 18 due to the lid being fully seated is not fully accommodated by the volume increase due to the penetration of the piston fully into the catch basin. Therefore, a slight over-pressure can occur in the inner vessel internal cavity when the lid is fully seated. This over-pressure helps drive the piston fully to the bottom of the catch basin and avoids any axially upward deformation of the piston due to unforseen pressure increases in the second chamber 106.

Figure 11:
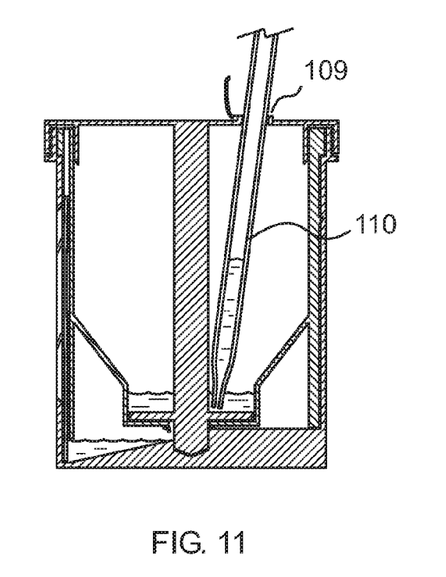

FIG. 11 shows that the aperture 109 in the lid can be opened and the remainder aliquot retrieved by a pipette 110 for confirmatory testing.

Figure 12:
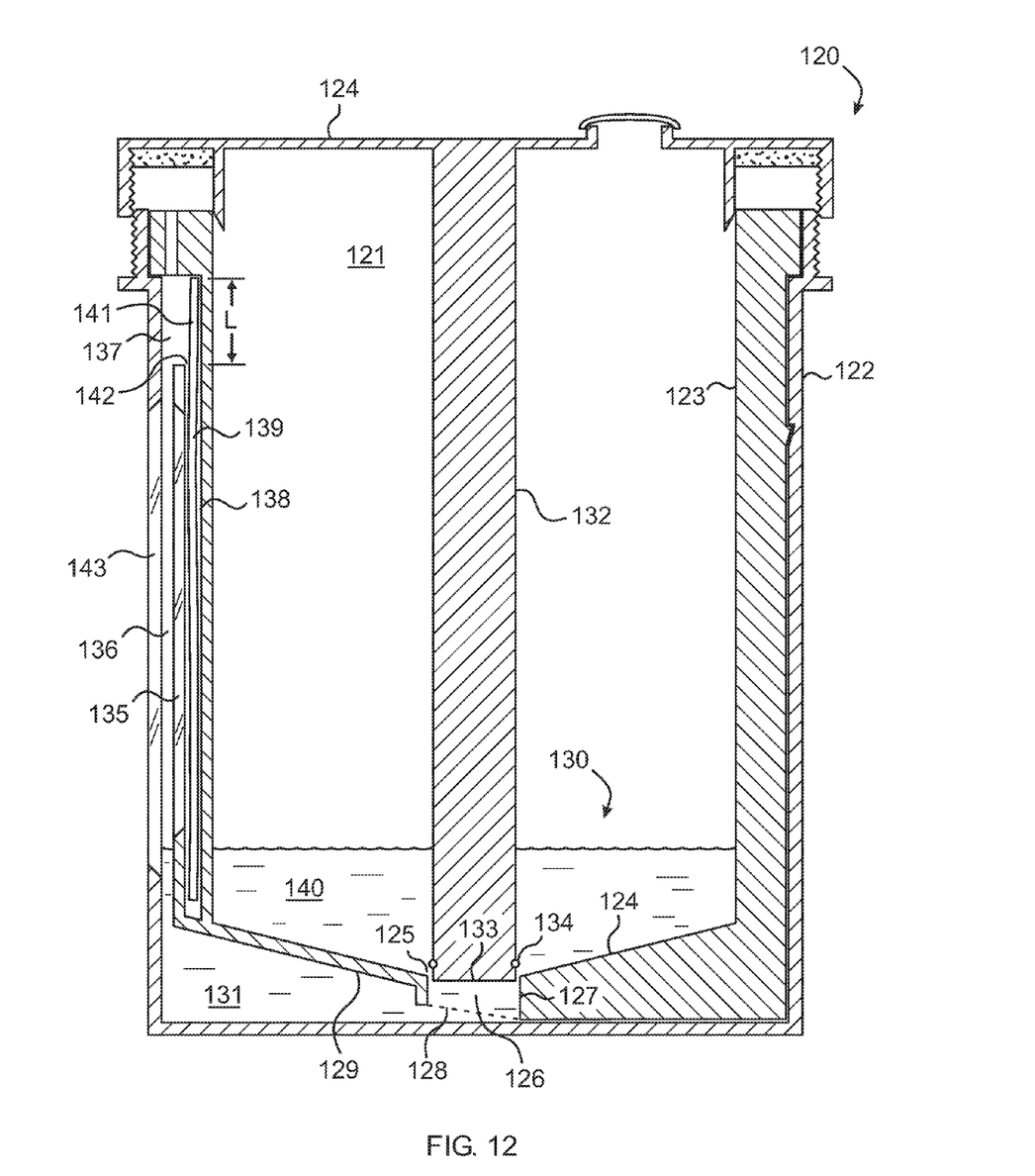
FIG. 12 is a diagrammatic cross-sectional side view of a first alternate specimen collection, preliminary screening, and confirmatory sample preservation device.

Referring now to FIG. 12, there is shown a cross-sectional view of an alternate cup 120 similar to the embodiment of FIG. 2 but with some differences as detailed below. The preliminary screening test is not initiated by fully screwing the lid upon the mated vessels; but rather when the cup is thereafter inverted.

The cup includes an outer vessel 122, an inner vessel 123 securely nested within the outer vessel, and a sealing lid 124. The inner vessel has a substantially cylindrical internal cavity 121 having a substantially frusto-conically shaped bottom surface 124 for draining liquid toward a central circular top opening 125 to a substantially cylindrical basin 126 having a substantially cylindrical sidewall 127. The bottom of the inner vessel forms a first chamber 130 at the bottom of the internal cavity of the inner vessel to contain the confirmatory aliquot. The basin has an elliptical bottom hole 128 formed by the gradual transition between a high termination of the cylindrical sidewall on one side opposite the other.

A liquid specimen 140 is deposited into the inner vessel and immediately flows through the hole 128 and starts filling a second chamber 131 formed between the inner and outer vessels. Once the second chamber is filled, additional liquid begins to fill the internal cavity 121 of the inner vessel 123. The liquid levels will reach equilibrium in both chambers and the liquid specimen remains contiguous.

The lid 124 has a central rod 132 extending downwardly from a proximal end attached to an undersurface of the lid to a piston structure 133 at its opposite, distal end. In this embodiment the piston structure has a circular periphery contiguous with the cylindrical surface of the rod. The piston structure has a circumferential O-ring 134 secured to its substantially cylindrical peripheral edge sized and oriented to intimately engage the basin sidewall 127 sealing the opening between the two chambers, thus separating the preliminary screening aliquot from the remainder aliquot preserved in the now sealed first chamber.

The test can then be initiated by turning the entire cup upside down, thereby allowing the preliminary screening aliquot to flow down a passageway 136 formed between the inner and outer vessels leading from the second chamber 131 to a reservoir 137 formed at one end of a number of substantially parallel pockets 138 each containing a testing strip 139. The pockets are analogous to the channels in the embodiment of FIG. 2. A sample pad end 141 of the strip extends a length L through an end aperture 142 to the pocket and into the reservoir. This length corresponds to the depth to which the strip end is immersed in liquid specimen during the preliminary screening test. Thus the depth can be selected to be at least the minimum depth required by the strip which requires the most depth.

It is understood that the undersurface 129 of the bottom of the inner vessel is slanted to form a ramp, thus directing the fluid toward the passageway.

The preliminary screening aliquot is substantially metered because once the specimen volume has filled the second chamber and begins to back up into the first chamber, additional liquid will primarily fill the first chamber with only a minor increase in the amount of preliminary screening aliquot as the level rises up the passageway 136 which has a minuscule volume compared with the entire volume held by the second chamber. The dimensions of the second chamber are selected to determine the minimum acceptable volume of the preliminary screening aliquot. Sealing of the basin by the piston thus apportions the two aliquots.

It should be noted that the pockets can be enclosed except for the aperture 142 through which extends the sample pad portion of the strips. A second viewing window 135 is provided on the radially outward part of the inner vessel 123 and in alignment with the first window 143 in the outer vessel 122. In this way the results of the preliminary screening test can be viewed through both windows.

Optionally, rather than using individual pockets, the inner vessel can be shaped and dimensioned similarly to the inner vessel in the embodiment of FIG. 2 to have an array of parallelly spaced apart channels for carrying the strips. Under this option the second viewing window 135 is not required. When the cup is in its upright orientation, the channels terminate at a lower end before reaching the bottom of the second chamber 131 so that the strips are not contacted by liquid until the cup is inverted. Once inverted, liquid can flow down a separate conduit analogous to the pressure equalizing vent 39 of the embodiment of FIG. 1. The conduit would allow passage of liquid from the second chamber to the reservoir exposing the sample pad portion of the strips to liquid specimen.

Figure 13:
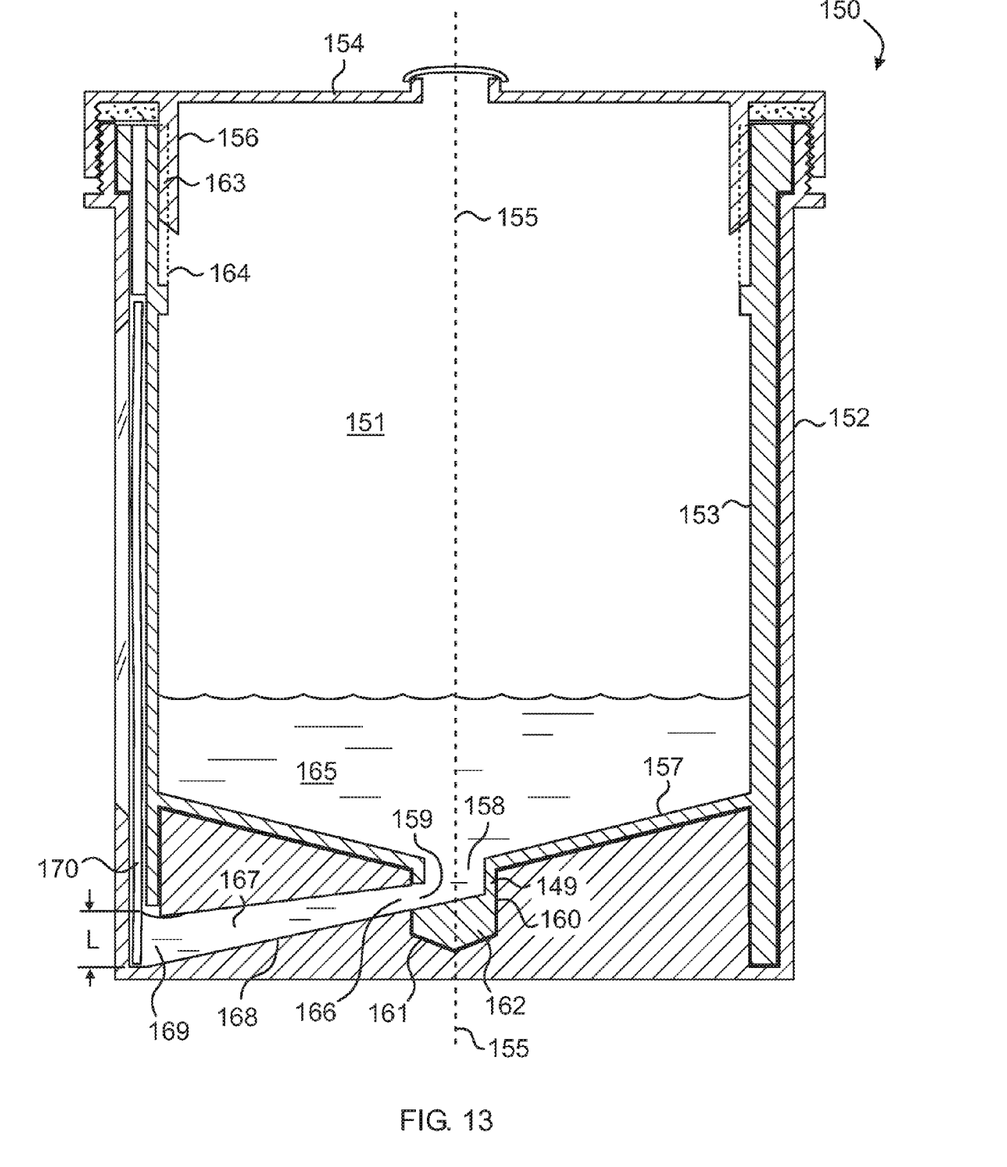
FIG. 13 is a diagrammatic cross-sectional side view of a second alternate specimen collection, preliminary screening, and confirmatory sample preservation device.

Referring now to FIG. 13, there is shown a cross sectional view of an alternate cup 150 similar to the embodiment of FIG. 2 having an outer vessel 152, an inner vessel 153, and a sealing lid 154, but with some differences as detailed below. The inner vessel can rotate with respect to the outer vessel about a common axis 155. The inner vessel has a central, substantially cylindrical cavity 151 forming a first chamber. A substantially frusto-conical bottom surface 157 leads toward the top opening of an apical basin 158. A radial hole 159 extends through a substantially cylindrical sidewall 149 of the basin 158. In a first orientation between the inner and outer vessels, the hole is blocked by the cylindrical sidewall 160 of a coaxial well 161 formed in the bottom of the outer vessel and coaxially engaged by a cylindrical rotational bearing 162.

A liquid specimen 165 is deposited into the inner vessel 153 partially filling it and the basin 158. Engaging the lid 154 seals the inner vessel first chamber. It is important to note that the annular wall 156 includes a number of crenelations 163 in its radially outward surface. The crenelations are shaped and dimensioned to intimately engage corresponding crenelations 164 formed into the radially inward facing surface of the inner vessel. The engaged crenelations act as a means for transferring torsional movement of the lid to the inner vessel. Thus, the preliminary screening test is initiated by rotating the inner vessel with respect to the outer vessel 152 about the rotation axis 155 by turning the lid. Rotation continues until the hole 159 lines up with an entry port 166 through the well side wall allowing fluid to flow through the hole and start to fill the second chamber 167. Once liquid reaches the second chamber it flows down a ramp 168 leading to a pool 169 for collecting the preliminary screening aliquot. The preliminary screening and remainder aliquot are separated by the continued rotation of the inner vessel until once again the hole is blocked and sealed by the well sidewall 160. Separation occurs before any back wash can occur from the second chamber back into the first chamber, thus preserving an uncontaminated aliquot for later confirmatory testing in the first chamber. The apportionment of the preliminary screening aliquot is accomplished by the dimensioning of the second chamber. The length L is selected to provide an adequate depth for the test strips 170. It shall be understood that some regions shown solid in the drawing can be readily adapted to be hollow to reduce material use. Care should be taken so that the various structures properly interlock while allowing the functions described above.

Figure 14:
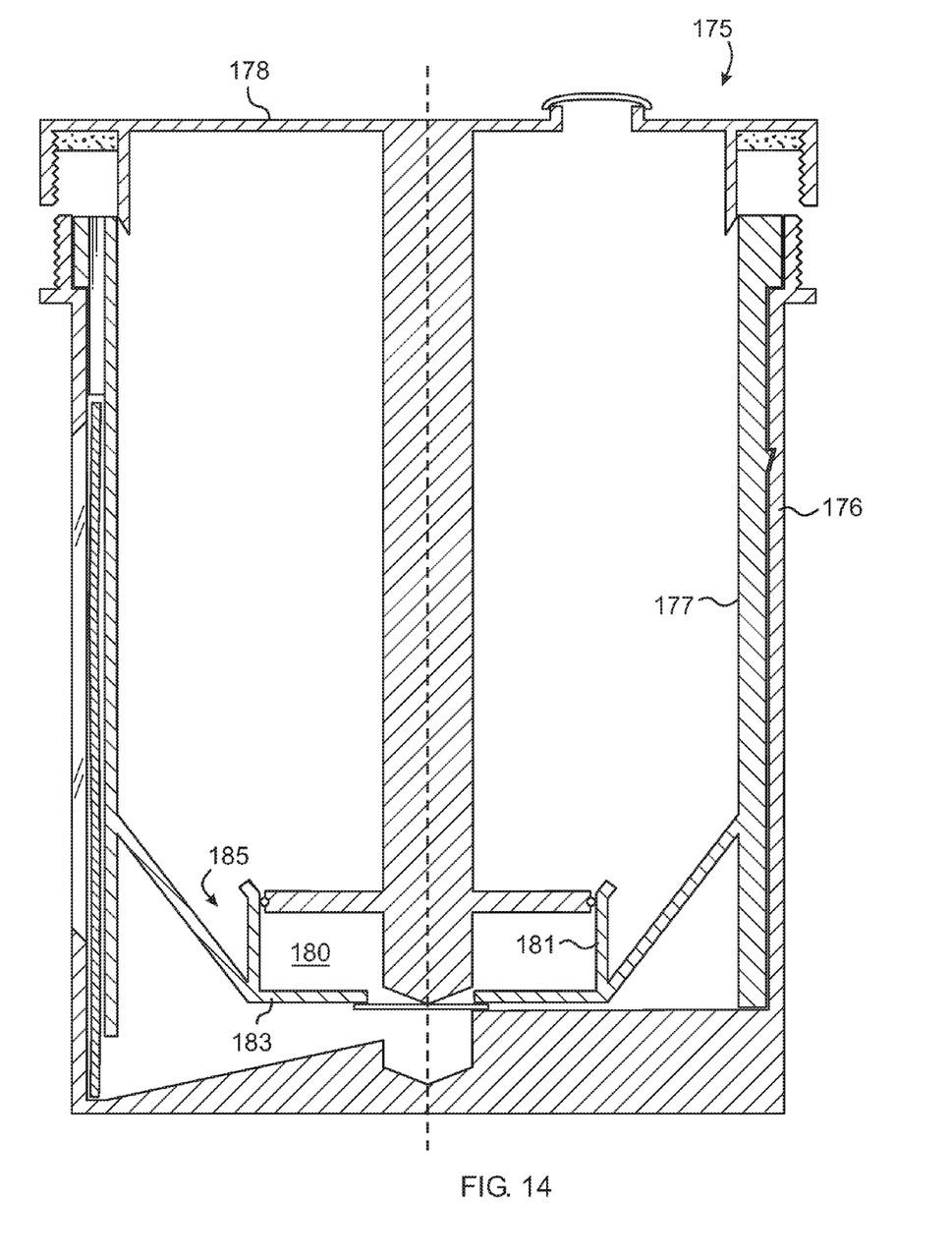
FIG. 14 is a diagrammatic cross-sectional side view of a third alternate specimen collection, preliminary screening, and confirmatory sample preservation device.

FIG. 14 there is shown a cross sectional view of an alternate cup 175 similar to the embodiment of FIG. 2 having an outer vessel 176, an inner vessel 177, and a sealing lid 178, but with some differences as detailed below. The side wall 181 of the basin 180 extends upwardly from the bottom 183 of the inner vessel 177 to form a substantially annular frusto conically shaped reservoir 185 surrounding the basin for trapping the remainder aliquot. The reservoir has a substantially frusto-conical shape to cause the remainder aliquot to collect against the outside wall of the basin side wall.

While the preferred embodiment of the invention has been described, modifications can be made and other embodiments may be devised without departing from the spirit of the invention and the scope of the appended claims.

What is claimed is:

1. A liquid specimen collecting, apportioning and testing device comprises:
    a first sealable chamber, said chamber being shaped and dimensioned to have a basin portion of a defined volume;
    said basin having a first opening and a bottom surface having a second opening sealed by an openable barrier;
    a second sealable chamber containing a number of preliminary screening strips;
    said defined volume being sufficient to supply an adequate amount of liquid specimen to all of said strips;
    a movable sealing and apportioning member shaped and dimensioned to seal said first opening; and,
    a barrier opener associated with said movable sealing member, said opener oriented to automatically open said barrier upon said movable sealing member sealing said first opening, thereby allowing fluid in said basin to flow into said second chamber and contact said strips; and,
    wherein said movable sealing and apportioning member has a lower surface shaped and dimensioned to intimately push out of said basin substantially all fluid sealed within said basin by said movable sealing member.

2. The device of claim 1, which further comprises said first chamber having an opening sealable by a lid.

3. The device of claim 2, wherein said sealing member is connected to said lid, whereby movement of said lid causes movement of said sealing member.

4. The device of claim 1, wherein said first chamber comprises a non-planar bottom portion having a section shaped to form said basin.

5. The device of claim 1, wherein said basin is substantially cylindrically shaped and said sealing member comprises a piston having a substantially circular face dimensioned to intimately engage said basin.

6. The device of claim 5, wherein said piston comprises said lower surface being shaped and dimensioned to intimately and substantially entirely contact said commensurately shaped bottom surface of said basin.

7. The device of claim 1, wherein said piston fully engaging said basin decreases the volume of said basin by said first volume.

8. The device of claim 5, wherein said opener comprises a spike extending axially from said piston, wherein said spike has a first axial length selected to allow penetration of said barrier after said piston has sealed said first opening.

9. The device of claim 8, wherein said second chamber is shaped and dimensioned to have a well located axially below said second opening; and wherein said spike is further shaped to nestingly mate with said well when said piston has fully engaged said basin.

10. The device of claim 1, wherein said device comprises an inner vessel and an outer vessel, wherein said second chamber is formed between an inner surface of said outer vessel and an outer surface of said inner vessel; and wherein said strips are carried within a number of channels formed between said inner surface and said outer surface.

11. The device of claim 10, wherein a sealable vent is formed between said second chamber and the outside of said device.

12. The device of claim 11, which further comprises an annular wall extending coaxially downward from an undersurface of said lid, said wall having an outer diameter commensurate with an inner diameter of said inner vessel.

* * * * *